United States Patent [19]

White

[11] 3,975,431

[45] Aug. 17, 1976

[54] PREPARING CARBOXYLIC ACIDS FROM GLYCIDONITRILES THROUGH ENOL ACYLATES

[75] Inventor: David R. White, Kalamazoo, Mich.

[73] Assignee: The Upjohn Company, Kalamazoo, Mich.

[22] Filed: Dec. 10, 1974

[21] Appl. No.: 531,433

Related U.S. Application Data

[63] Continuation-in-part of Ser. No. 271,389, July 13, 1972, abandoned.

[52] U.S. Cl. ................. 260/515 R; 260/514 R; 260/515 A; 260/540; 260/520 R
[51] Int. Cl.² ............................................. C07C 63/52
[58] Field of Search ............. 260/515 R, 514 R, 540

[56] References Cited
OTHER PUBLICATIONS

Stork et al., J.A.C.S., 82, pp. 4315–4323 (1960).
Wagner et al., Synthetic Organic Chem., John Wiley & Sons, Inc., New York, N. Y., pp. 35–39, 169–170, & 481–483 (1965).
Contacuzene et al., "Tetrahedron Letters," pp. 2237–2242 (1966).

Primary Examiner—James O. Thomas, Jr.
Assistant Examiner—G. Breitenstein
Attorney, Agent, or Firm—John T. Reynolds

[57] ABSTRACT

Process for preparing carboxylic acids by converting a glycidonitrile to the enol acylate via hydrohalogenation, acylation and dehydrohalogenation procedures, and conversion of the enol acylate to the carboxylate salt with a base and of the salt to the carboxylic acid with acid. Cyanide content in the mixture is destroyed by adding persulfate or hypochlorite salts. This process, can be used, e.g., to prepare 2-(4'-isobutylphenyl)propionic acid, now known generically as ibuprofen, a highly active anti-inflammatory drug, as well as a host of other useful carboxylic acids.

3 Claims, No Drawings

PREPARING CARBOXYLIC ACIDS FROM GLYCIDONITRILES THROUGH ENOL ACYLATES

CROSS REFERENCE

This application is a continuation-in-part of application Ser. No. 271,389, filed July 13, 1972, now abandoned.

BACKGROUND OF THE INVENTION

Prior art carboxylic acid syntheses from aromatic ketones by the addition of hydrogen cyanide such as that disclosed by Eliel et al. Org. Syn. 33, 7 (1953) involve a reversible step with an unfavorable equilibrum as well as a reduction step. In the process of the present invention the steps are irreversible and no reduction step is required. The process of the present invention thus results in greatly increased yields and higher purity of the desired carboxylic acid. The carboxylic acids which are produced by the process of this invention are known in the art as useful compounds. For example, 2-(p-isobutylphenyl)propionic acid and 2-(m-fluoro-p-phenyl)phenylpropionic acid are highly active antiinflammatory agents, and 3,4-dimethoxyphenylacetic acid is useful in preparing papaverine.

SUMMARY OF THE INVENTION

The novel process of this invention is illustratively represented by the following reaction sequence:

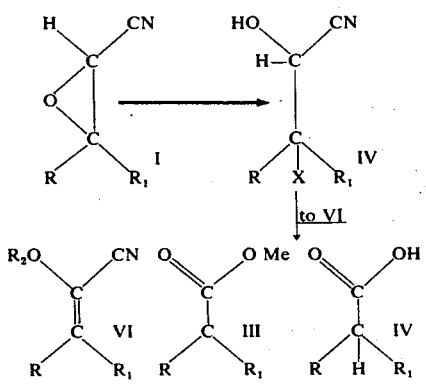

wherein in the above formulae when taken separately R represents hydrogen, an aliphatic, alicyclic, aromatic or heterocyclic group and $R_1$ when taken separately represents an aliphatic, alicyclic, aromatic or heterocyclic group; R and $R_1$ when taken together and connected represent an alicyclic or heterocyclic group, $R_2$ is the acyl radical of the acylating agents, as described hereinbelow. $Me^+$ is an alkali metal selected from the group consisting of sodium, potassium and lithium; and X is selected from the group consisting of chloro, bromo and iodo.

Included among the aliphatic, alicyclic and aromatic groups which R and $R_1$ can each represent when taken separately are, for example, alkyl (including saturated and unsaturated, straight and branched chain alkyl and cycloalkyl) and aryl (including alkaryl and aralkyl) radicals, such as methyl, ethyl, propyl, isopropyl, n-butyl, sec. butyl, tert-butyl, amyl, hexyl, heptyl, octyl, decyl, dodecyl, octadecyl, vinyl, allyl, methallyl, butenyl, pentenyl, hexenyl, heptenyl, octenyl, ethynyl, propynyl, butynyl, pentynyl, hexynyl, heptynyl, octynyl and isomeric forms thereof, cyclobutyl, cyclopentyl, cyclohexyl, 1-cyclohexenyl, methylcyclohexyl, cycloheptyl, cyclooctyl, cyclodecyl, cycloundecyl, cyclododecyl, cyclopentadecyl, henyl, tolyl, xylyl, benzyl, phenethyl, phenylpropyl, benzhydryl, naphthylmethyl, o-carboxylbenzyl, and the like, as well as fused and bridged ring structures, such indanyl, indenyl, naphthyl, acenaphtyl, phenanthryl, cyclopentanopolyhydrophenanthryl, adamantanyl, bicyclo[3:1:1]heptyl, bicyclo[2:2:2]octyl and the like; all of which can either be unsubstituted or substituted with one or more non-interfering substituents, such as hydroxyl derivatives, for example, alkoxy such as methoxy, ethoxy, propoxy, butoxy, and the like; acyloxy, such as acetoxy, propionoxy, butyroxy and the like; nitro groups; amino groups; alkylamino groups, such as methylamine, ethylamino, dimethylamino and the like; halogens, such as fluorine, chlorine, or bromine; carbonyl derivatives such as enol ethers and ketals; and the like.

Included among the heterocyclic groups which R and $R_1$ can represent are substituted and unsubstituted azabicycloalkane groups such as azabicyclo [3.2.2] octyl and azabicyclo [3.2.1] nonyl and the like, furfuryl groups, tetrahydrofurfuryl groups, piperidyl groups, pyrrolidyl groups, pyridyl groups, thiophene groups, alkaloid nuclei groupings containing for example indole, dihydroindole, quinolidine, quinthio groups and the like.

Included among the alicyclic and heterocyclic groups in which $R_1$ and $R_2$ when taken together and connected can represent, are cyclopropyl, cyclobutyl, cyclohexyl, dicyclohexyl, cyclodecyl, cyclododecyl, cyclopentadecyl, and the like) piperidyl, pyrrolidyl, and the like; fused ring systems such as cyclopentanopolyhydrophenanthranyl, indanyl, indenyl, and the like, bridged ring systems such as adamantyl, bicyclo [2.2.1] heptyl, bicyclo [2.2.2] octyl, bicyclo [3.2.2] nonyl, azabicycloalkyls, and the like, all of which can be substituted by non-interfering substituents such as those hereinbefore named.

Certain of the intermediates falling within the scope of formula VI, above, exist in either the cis configuration, the trans configuration or mixtures thereof. However, for the purpose of carrying out the process of this invention the stereo configuration of the compounds of formula VI is not important since both the cis and trans forms react in the subsequent process steps of this invention to produce the desired products (IV).

DETAILED DESCRIPTION OF THE INVENTION

The starting glycidonitriles of formula I are either known in the art or can be prepared from known ketones and aldehydes by a Darzens condensation, for example in accordance with the procedure disclosed by V. F. Martynov and A. V. Schelkunov, J. Gen. Chem. USSR 27, 1271–3 (1957). In preparing the necessary starting materials, a ketone or aldehyde of formula VII;

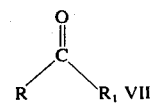

wherein R and $R_1$ have the same meanings given above, is reacted with chloroacetonitrile in the presence of a strong base such as sodium methoxide, potassium t-butoxide, sodium t-amylate and the like. The reaction is carried out in a non-polar aprotic solvent such as xylene, toluene, hexanes, petroleum ethers and the like, preferably at a relatively low temperature, such as from about −10° to about +10° C., for a period of from about 1 to 5 hours. In our preferred operation of this step we use sodium hydroxide in a mixture of dimethylformamide and toluene. The glycidonitrile (I) thus obtained is recovered and purified by conventional methods, for example, by distillation under reduce presure.

In carrying out the process of this invention the glycidonitriles of formula I are subjected to the following reaction steps:

The selected glycidonitrile is dissolved or suspended in a suitable inert organic solvent such as — hexanes, petroleum ethers, diethyl ether, xylene, toluene, Skellysolve V and the like, or mixtures thereof, — and treated with a hydrogen halide selected from the group consisting of hydrogen chloride, hydrogen bromide, and hydrogen iodide to obtain the corresponding 2-hydroxy-3-halopropionitrile (V). In carrying out the reaction the hydrogen halide can be used under anhydrous or aqueous conditions. In the preferred embodiment, the hydrogen halide is used in a slight excess of the theoretically required amount. Anhydrous conditions are preferred. The reaction period is from about 1 to 8 hours, depending on the particular starting material employed and the temperature at which the reaction is carried out. Temperatures of from about 20° to about 60° C. are generally preferred, but the reaction is operative at higher and lower temperatures. When the reaction is carried out under aqueous conditions the aqueous phase is removed and the organic phase containing the intermediate compound V is dried by conventional methods, for example, by azeotropic distillation or over a drying agent such as anhydrous sodium sulfate etc., magnesium sulfate, sodium carbonate and the like. When anhydrous conditions are employed, compound V is used directly in the next step without isolation from the reaction medium.

The 2-hydroxy-3-halopropionitrile (V) is then subjected to acylation and dehydrohalogenation in accordance with procedures well known in the art to obtain the corresponding enol acylates of formula VI. For example, the selected 2-hydroxy-3-halopropionitrile compound V is treated with excess acid anhydride or acid halide at about room temperature for a period of from about 1 to about 24 hours in the presence of a tertiary amine such as pyridine, triethyl amine, lutidine, N-methylmorpholine, N,N-dimethylaniline and the like. Suitable acylating agents are the acid anhydrides or acid halides or organic carboxylic acids containing from 1 to 18 carbon atoms; for example, saturated and unsaturated aliphatic acids and aromatic acids such as acetic, propionic, butyric, isobutyric, tert.-butylacetic, valeric, isovaleric, caproic, caprylic, decanoic, dodecanoic, acrylic, crotonic, hexynoic, heptnoic, octynoic, cyclobutanecarboxylic, cyclopentanecarboxylic, cyclohexanecarboxylic, dimethylcyclohexanecarboxylic, benzoic, toluic, naphthoic, ethylbenzoic, phenylacetic, naphthaleneacetic, phenylvaleric, cinnamic, phenylpropiolic, phenylpropionic, p-butoxyphenylpropionic, succinic, glutaric, dimethylglutaric, maleic, cyclopentylpropionic, myristic, palmitic and stearic acids. The dehydrohalogenation is carried out by adding an excess of anhydrous base following the acylation step. Bases which can be used include the tertiary amines disclosed above as esterification catalysts, as well as other bases such as sodium hydride, sodium amide, sodium t-butoxide, sodium t-amylate as well as mixtures of a catalytic amount of a trialkylamine and a larger amount (at least stoichiometrically equivalent to the hydrogen halide content) of an alkali metal carbonate, which reacts to form the alkali metal halide and regenerates the trialkylamine, and the like. In the preferred embodiment, the dehydration is carried out under reflux temperatures for a period of from about 1 to about 24 hours, or alternatively an excess of the selected base can be added and the dehydration can be carried out simultaneously with the acylation step. The enol acylates of formula VI, thus obtained are, if desired, recovered from the reaction mixture and purified by conventional methods or preferably they are used directly in the next step without recovery from the reaction medium.

The enol acylates VI are then subjected to hydrolysis under basic conditions, preferably in the presence of an alkali metal base such as sodium hydroxide, potassium hydroxide, lithium hydroxide, sodium carbonate, potassium bicarbonate and the like to obtain the alkali metal salt of the corresponding carboxylic acid (III). The hydrolysis is carried out within a broad temperature range, for example from about 0° to about 100° C., for a period of from about 1 to about 24 hours. However, temperatures within the range of from about 40° to 80° C. are preferred. The carboxylic acid alkali metal salt is recovered and purified by conventional methods, for example, chromatography and/or crystallization from a suitable solvent such as methylene chloride, ethyl acetate, xylene, toluene, hexanes, benzene and the like or by distillation under reduced presure, or used in the next step without recovery from the reaction medium.

The sodium salt (III) thus obtained, is then subjected to acidification with a strong acid, for example, hydrochloric acid, sulfuric acid, phosphoric acid, trifluoroacetic acid, p-toluenesulfonic acid, benzenesulfonic acid, methanesulfonic acid and the like to obtain the corresponding free acid (IV). The acidification is carried out within a broad temperature range such as from about 0° C. or lower to the boiling point of the reaction mixture. The product (IV), thus obtained, is recovered from the reaction mixture and purified by conventional methods. For example, the product is extracted from the reaction mixture in a suitable solvent such as Skellysolve B hexanes, toluene, xylene, ethyl acetate, benzene, methylene chloride, chloroform, and the like and crystallized, if the product is a solid. If the product is a liquid it is recovered and purified by distillation, preferably at reduced pressure.

None of the intermediates need to be isolated and purified. The entire process can be conveniently carried out in a one pot operation.

The following preparation and Examples illustrate the best mode contemplated for carrying out the invention, but are not to be construed as limiting the scope thereof.

PREPARATION A

3-Methyl-3-(p-isobutylphenyl)glycidonitrile (I)

A mixture of 17.6 g. of p-isobutylacetophenone (VII) and 61 ml. of a 15.4% w/v solution of chloroacetonitrile in xylene is cooled to about −10° C. and a solution of sodium t-amylate (prepared by stirring 4.45 g. of sodium amide and 10.0 g. of t-amyl alcohol in 150 ml. of xylene at 60° C. for about 4 hours) is added with stirring over a period of about 15 minutes keeping the temperature at about −5° C. Stirring is continued for an additional period of about 1 hour and then 70 ml. of water is added. The reaction mixture is then filtered and the organic (xylene) phase is separated. The aqueous layer is extracted with 30 ml. of xylene and the xylene solutions are combined, dried over anhydrous sodium sulfate and concentrated. The residue thus obtained is distilled (105° C./.05 mm.) to give 18.88 g. (88% yield) of 3-methyl-3-(p-isobutylphenyl)-glycidonitrile (I) as an oil.

EXAMPLE 1

2-(p-isobutylphenyl)propionic acid (IV)

A solution of 7.87 g. (36.6 mmole) of the 3-methyl-3-(p-isobutylphenyl)glycidonitrile, from Preparation A, in 60 ml. of toluene is treated with 40 mmole of dry hydrogen chloride (10.7 ml. 3.71 N HCl in ether) and stirred for about 1 hour to give 2-hydroxy-3-methyl-3-(p-isobutylphenyl)-3-chloropropionitrile (V) as shown by TLC (thin-layer chromotography). The reaction is then treated with 3.64 g. (46 mmole) of pyridine and 4.30 g. (42.2 mmole) of acetic anhydride. The reaction mixture is stirred for about 2½ hours to give the corresponding chloroacetate. Triethylamine [5.04 g. (50 mmole)] is then added and the mixture is held at reflux for about 20 hours. TLC shows a mixture of the cis and trans isomers of 2-acetoxy-3-(p-isobutylphenyl)acrylonitrile (VI). If desired the intermediate thus obtained can be isolated by washing with aqueous acid and then drying the toluene solution over anhydrous sodium sulfate and concentration at reduced pressure to a mixture of cis and trans isomers of 2-acetoxy-3-methyl-3-(p-isobutylphenyl)acrylonitrile (VI), as an oil, ultraviolet spectrum (methanol), $\lambda$max, 212m$\mu$ ($\epsilon$=10,730) and 263m$\mu$ ($\epsilon$=13,500); NMR (nuclear magnetic resonance) and IR (infrared) spectra support the structure.

Alternatively, the toluene solution of the intermediate (VI) is diluted with 16 ml. of methanol and 12 ml. of 50% aqueous sodium hydroxide solution and the mixture is stirred at reflux for about 16 hours. The two phases are then separated while warm and the toluene phase is extracted with 25 ml. of aqueous 5% sodium hydroxide solution to give an aqueous alkaline solution containing the sodium salt of 2-(p-isobutylphenyl)propionic acid (III). The aqueous hydroxylic phases are combined, acidified with about 30 ml. of concentrated hydrochloric acid and extracted with two 50 ml. portions of ethyl acetate. The ethyl acetate extracts are combined, dried over anhydrous sodium sulfate, decolorized with 1 g. of activated charcoal (Darco), filtered and concentrated to give 7.57 g. of oil which is diluted with 15 ml. of Skellysolve B hexanes, seeded and cooled at 50° C. for about 2 hours. The crystalline solid thus obtained is collected on a filter and washed with 10 ml. of hexanes to give 4.836 g. of 2-(p-isobutylphenyl)propionic acid (IV), melting at 74.0°–75.5° C.; NMR and IR supports the assigned structure.

Anal. Calcd. for $C_{13}H_{18}O_2$: C, 75.69; H, 8.79. Found: C, 75.82; H, 8.78.

A second fraction obtained from the mother liquors gives 0.712 g. of 2-(p-isobutylphenyl)propionic acid (IV), melting at 73.0°–74.5° C.

Following the procedure of Preparation A and Example 1 above, other glycidonitriles of formula (I) can be converted to the corresponding carboxylic acids of formula (IV). The following conversions are representative:

3,4-dihydrospiro[naphthalene-1(2H),2'-oxirane]-3'-carbonitrile to obtain 1,2,3,4-tetrahydro-1-naphthoic acid, 17$\beta$-acetoxyspiro[androstane-3,2'-oxirane]-3'-carbonitrile to obtain 17$\beta$-acetoxyandrostane-3$\beta$-carboxylic acid, Spiro[adamantane-2,2'-oxirane]-3'-carbonitrile to obtain 2-adamantanecarboxylic acid, $\beta$-phenylcyclohexylglycidonitrile to obtain $\alpha$-phenylcyclohexaneacetic acid, 3,3-diphenylglycidonitrile acid to obtain diphenylacetic acid, 1,2,3,4-tetrahydrospiro[anthracene-9(10H),2'-oxirane]-3'-carbonitrile to obtain 1,2,3,4,9,10-hexahydro-9-anthroic acid, tetrahydrospiro[oxirane-2,4'-[4H]pyran]-3-carbonitrile to obtain tetrahydro-4H-pyran-4-carboxylic acid, and spiro[1H-2-benzopyran-4(3H),2'-oxirane]-3'-carbonitrile to obtain 3,4-dihydro-1H-2-benzopyran-4-carboxylic acid.

PREPARATION B

1-oxospiro[2,5]octane-2-carbonitrile

A solution of 19.6 g. of cyclohexanone and 16.5 g. of chloroacetonitrile in toluene is cooled with stirring to about −10° C. and treated dropwise with a solution of sodium t-amylate (prepared by stirring 8.58 g. of sodium amide, 19.3 g. of t-amyl alcohol and 300 ml. of toluene for 2 hours at 50° C.) over a period of about 45 minutes, keeping the reaction temperature at about −10° to about −5° C. After the addition is complete the reaction mixture is stirred for about 1 hour at about 0° C., diluted with 100 ml. of water and allowed to separate. The aqueour phase is removed and extracted with 50 ml. of toluene. The toluene (organic) phases are combined, washed with brine, dried over anhydrous sodium sulfate and concentrated to give 24.4 g. (89% yield) of the corresponding glycidonitrile, 1-oxospiro[2.5]octane-2-carbonitrile, (I) as an oil.

EXAMPLE 2

Cyclohexanecarboxylic acid

A solution of 6.84 g. of the glycidonitrile, 1-oxospiro[2.5]octane-2-carbonitrile (Preparation B) thus obtained in 40 ml. of toluene is treated with dry hydrogen chloride (14.6 ml. of 3.71 N hydrogen chloride in ether), stirred at about 26° C. for 4 hours and then at 45° C. for an additional 2.5 hours to give 1-chlorocyclohexaneglycolonitrile (V). The reaction mixture is then treated with 4.97 g. of pyridine, 4.47 ml. of acetic anhydride and 9.45 ml. of triethylamine and stirring is continued keeping the temperature at about 75° C. for about 16 hours. The reaction mixture is then cooled, washed with two 40 ml. portions of 2 N hydrochloric acid and then with water. The toluene is then removed and the product distilled to give an 87% yield of the corresponding 2-acetoxyacrylonitrile (VI) ($\Delta^{1,\alpha}$ - cyclohexaneglycolonitrile, acetate) b.p. 89°–94° C./0.6 mm. Hg.; IR and NMR spectra support the assigned structure.

Alternatively the toluene solution obtained above is mixed with 15 ml. of water, 6 ml. of acetone and 12 ml. of aqueous 50% sodium hydroxide solution and stirred overnight at about 50° C. to give the sodium salt of cyclohexanecarboxylic acid (III). The reaction mixture is then cooled and the phases separated. The toluene phase is washed with 10 ml. of 5% aqueous sodium hydroxide. The phase and wash are combined, backwashed with 25 ml. of toluene, acidified with about 17 ml. of 12 N sulfuric acid and extracted with Skellysolve B hexanes (2 × 50 ml.). The combined extracts are dried over anhydrous sodium sulfate, concentrated and the residue is distilled (154°–159° C./54 mm. Hg.) to give 4.382 g. (64% yield) of cyclohexanecarboxylic acid (IV), IR and NMR spectra are identical with those of an authentic sample of cyclohexanecarboxylic acid.

PREPARATION C (3-methyl-3-n-propylglycidonitrile)

A solution of 17.2 g. of 2-pentanone (VII) and 16.5 g. of chloroacetonitrile in 20 ml. of toluene is treated with sodium t-amylate and worked up in the manner described in Example 2, above, to give a toluene solution of the corresponding glycidonitrile (I) (3-methyl-3-n-propylglycidonitrile).

EXAMPLE 3

2-Methylvaleric Acid (IV)

The toluene solution of (3-methyl-3-n-propylglycidonitrile (Preparation C) is treated with dry hydrogen chloride (59.3 ml. of 3.71 N HCl in ether) with stirring for about 4 hours at 45°C. A mixture of 21.1 g. of pyridine, 18.2 ml. of acetic anhydride and 38.5 ml. of triethyl amine is then added and the reaction mixture is stirred at 75° C. for about 16 hours. The reaction mixture is then cooled, washed with 2 N hydrochloric acid (2 × 160 ml.) and then with 100 ml. of water. The intermediate thus obtained can if desired be isolated by drying and concentrating the toluene solution or alternatively, the toluene solution is mixed with 61 ml. of water, 24 ml. of acetone and 48 ml. of aqueous 50% sodium hydroxide solution and stirred at about 50° C. overnight to give the sodium salt of 2-methylvaleric acid (III), the reaction mixture is then cooled and the two phases are separated. The toluene phase is washed with 10 ml. of 5% aqueous sodium hydroxide solution. The alkali phase and wash are combined and backwashed with 25 ml. of toluene. The alkaline phase is then acidified with 12 N sulfuric acid and extracted with Skellysolve B hexanes, (2 × 50 ml.). The hexane extracts are combined and dried over anhydrous sodium sulfate; the solvent is removed and the product distilled under vacuum to give 17.4 g. (75% yield) of 2-methylvaleric acid (IV), b.p. 186° C./760 mm. Hg.

PREPARATION D 3-(3,4-dimethoxyphenyl)glycidonitrile

A solution of 33.1 g. of 3,4-dimethyloxybenzaldehyde and 16.5 g. of chloroacetonitrile in 20 ml. of toluene is treated with sodium t-amylate and worked up in the manner described in Example 3, above, to give a toluene solution of 3-(3,4-dimethoxyphenyl) glycidonitrile (I).

EXAMPLE 4

3,4-dimethoxyphenylacetic acid

The toluene solution of the 3-(3,4-dimethoxyphenyl)glycidonitrile (Preparation D) is treated with dry hydrogen chloride (59.3 ml. of 3.71 N HCl in ether) with stirring for about 4 hours at 45° C. A mixture of 21.1 g. of pyridine, 18.2 ml. of acetic anhydride and 38.5 ml. of triethyl amine is then added and the reaction mixture is stirred at 75° C. for about 16 hours. The reaction mixture is then cooled, washed with 2 N hydrochloric acid (2 × 160 ml.) and then with 100 ml. of water. The intermediate 2-acetoxy-3-(3,4-dimethoxyphenyl)acrylonitrile (VI) thus obtained, can if desired be isolated by drying and concentrating the toluene solution. Alternatively, the toluene solution is mixed with 61 ml. of water, 24 ml. of acetone and 48 ml. of aqueous 50% sodium hydroxide solution and stirred at about 50° C. overnight to give the sodium salt of 3,4-dimethoxyphenylacetic acid (III). The reaction mixture is then cooled and the two phases are separated. The toluene phase is washed with 10 ml. of 5% aqueous sodium hydroxide solution. The alkaline phase and wash are combined and backwashed with 25 ml. of toluene. The alkaline phase is acidified with 12 N sulfuric acid and extracted with Skellysolve B hexanes, (2 × 50 ml.). The hexane extracts are combined and dried over anhydrous sodium sulfate; the solvent is removed and the product distilled under vacuum to give 3,4-dimethoxyphenyl acetic acid m.p. 96°–98° C.

PREPARATION E

A solution of 17.2 g. of valeraldehyde and 16.5 g. of chloroacetonitrile in 20 ml. of toluene is treated with sodium t-amylate and worked up in the manner described in Example 3, above, to give a toluene solution of 3-butylglycidonitrile (I).

EXAMPLE 5

Hexanoic Acid

The toluene solution of the 3-butylglycidonitrile (Preparation E) is treated with dry hydrogen chloride (59.3 ml. of 3.71 N HCl in ether) with stirring for about 4 hours at 45° C. A mixture of 21.1 g. of pyridine, 18.2 ml. of acetic anhydride and 38.5 ml. of triethyl amine is then added and the reaction mixture is stirred at 75° C. for about 17 hours. The reaction mixture is then cooled, washed with 2 N hydrochloric acid (2 × 160 ml.) and then with 100 ml. of water. The intermediate 2-acetoxy-3-butylacrylonitrile (2-acetoxy-2-heptenonitrile) (VI) thus obtained can if desired be isolated by drying and concentrating the toluene solution or alternatively, the toluene solution is mixed with 61 ml. of water, 24 ml. of acetone and 48 ml. of aqueous 50% sodium hydroxide solution and stirred at about 50° C. overnight to give the sodium salt of hexanoic acid (III). The reaction mixture is then cooled and the two phases are separated. The toluene phase is washed with 10 ml. of 5% aqueous sodium hydroxide solution. The alkaline phase and wash are combined and backwashed with 25 ml. of toluene. The alkaline phase is acidified with 12 N sulfuric acid and extracted with Skellysolve B hexanes, (2 × 50 ml.). The hexane extracts are combined and dried over anhydrous sodium sulfate; the solvent is removed and the product distilled under vacuum to give hexanoic acid (IV).

EXAMPLE 6

2-(m-fluoro-p-phenyl)phenylpropionic acid

Following the procedure of Preparation A and Example 1 above, but substituting a stoichiometric equivalent amount of m-fluoro-p-phenylacetophenone as starting material in place of p-isobutylacetophenone gives 2-methyl-2-(m-fluoro-p-phenyl) phenylglycidonitrile which is converted by the procedure of Example 1 to obtain 2-(m-fluoro-p-phenyl)phenylpropionic acid.

In the process of this invention the glycidonitrile is converted to the acid through the described series of steps without rearrangement or migration of the substituents on the glycidonitrile carbon skeleton. Thus, for example, when the process is applied to the production of 2-(4'-isobutylphenyl)propionic acid the arrangement of the substituents on the numbered carbon atom skeleton can be illustrated as follows:

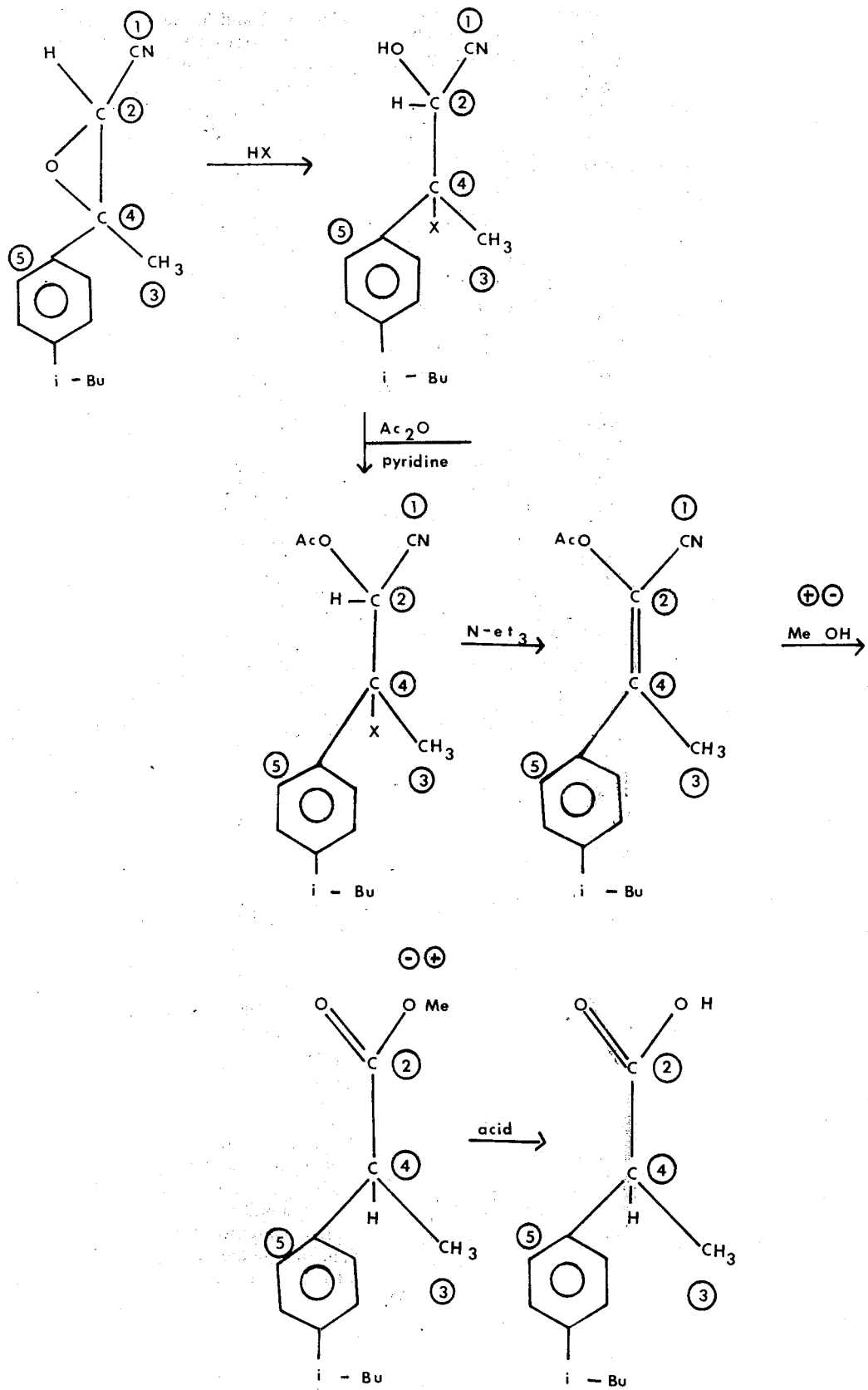

wherein i-Bu denotes the isobutyl group, AcO denotes an acyloxy group, e.g., from, acetic anhydride, N-et₃ denotes triethylamine, and Me⁺ denotes the cation from the strong base. Thus, by this process for preparing carboxylic acids the cyano carbon is expelled and carbon 2 remains attached to the unchanged carbon skeleton chain 3, 4 and 5 at carbon 4 throughout the process. In other words, carbons 2, 3, 4 and 5 which survive in the product do not change their relative positions.

This process has the advantage over other carboxylic acid making processes based upon the use of an ionic Lewis acid to react with the glycidonitrile in that it eliminates the generation and resulting evolution of gaseous hydrogen cyanide which is given off in that process as when intermediates dimerize. By this process the cyanide content in the reaction mixture remains dissolved and in the mixture can be easily treated with cyanide ion destorying substances to obviate the necessity for concern for the possible presence of hydrogen cyanide vapors.

Thus, the process of this invention offers the advantage over processes based upon the chemical action of ionic Lewis acids such as lithium perchlorate, potassium bisulfate, or the like upon glycidonitriles by permitting the operation of the process so that the cyanide ion derived from the glycidonitrile starting material is converted in this process to an alkali metal cyanide which remains dissolved or suspended in the reaction mixture vessel, wherein the cyanide ion can be destroyed by addition of an appropriate cyanide ion destroying substance such as an alkali metal or ammonium persulfate or hypochlorite salt.

I claim:
1. The process for the production of a carboxylic acid of the formula:

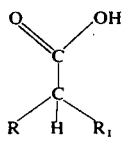

wherein R when taken separately represents hydrogen or an aliphatic, or aromatic group and R₁ when taken separately represents an aliphatic or aromatic group; and R and R₁ when taken together and connected represents an alicyclic group, which comprises:
 1. treating a glycidonitrile of the formula:

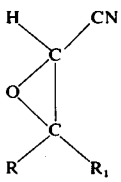

wherein R and R₁ have the meaning given, above, with a hydrogen halide selected from the group consisting of hydrogen chloride, hydrogen bromide and hydrogen iodide to obtain a 2-hydroxy-3-halopropionitrile of the formula:

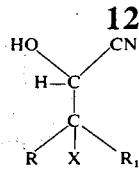

wherein R and R₁ have the meanings given, above, and X is selected from the group consisting of chloro, bromo, and iodo;
 2. acylating and dehydrohalogenating the 2-hydroxy-3-halopropionitrile thus obtained to obtain an enol acylate of the formula:

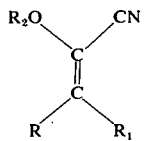

wherein R and R₁ have the meanings given, above, and R₂ is the acyl radical of an organic carboxylic acid;
 3. subjecting the enol acylate so obtained to hydrolysis with an aqueous alkali metal base to obtain an alkali metal salt of a carboxylic acid of the formula:

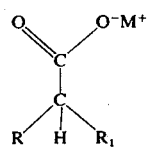

wherein R and R₁ have the meanings given, above, and M⁺ is selected from the group consisting of sodium, potassium, and lithium, and
 4. acidifying the alkali metal salt of the carboxylic acid so obtained with a strong acid to obtain the corresponding free carboxylic acid.

2. Process in accordance with claim 1 wherein R is aromatic and R₁ is aliphatic.

3. Process in accordance with claim 2 for the production of 2-(p-isobutylphenyl)-propionic acid which comprises:
 1. treating 3-methyl-3-(p-isobutylphenyl)glycidonitrile with a hydrogen halide selected from the group consisting of hydrogen chloride, hydrogen bromide and hydrogen iodide, to obtain the corresponding 2-hydroxy-3-methyl-3-(p-isobutylphenyl)-3-halopropionitrile;
 2. acylating and dehydrohalogenating the 2-hydroxy-3-methyl-3-(p-isobutylphenyl)-3-halopropionitrile thus obtained to produce the corresponding 2-acryloxy-3-methyl-3-(p-isobutylphenyl)acrylonitrile;
 3. subjecting the 2-acyloxy-3-methyl-3-(p-isobutylphenyl)acrylonitrile thus produced to hydrolysis with an aqueous alkali metal base to obtain the corresponding alkali metal salt of 2-(p-isobutylphenyl)propionic acid; and
 4. acidifying the salt thus obtained with a strong acid to produce 2-(p-isobutylphenyl)propionic acid.

* * * * *